(12) United States Patent
Srinivasan

(10) Patent No.: US 6,732,943 B2
(45) Date of Patent: May 11, 2004

(54) METHOD OF GENERATING UNIFORM PORES IN THIN POLYMER FILMS

(75) Inventor: Sudarsan Srinivasan, Fremont, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

(21) Appl. No.: 09/828,712

(22) Filed: Apr. 5, 2001

(65) Prior Publication Data

US 2003/0025008 A1 Feb. 6, 2003

(51) Int. Cl.$^7$ .............................. B05B 17/00; B65D 1/32
(52) U.S. Cl. .................... 239/1; 239/327; 239/567; 239/602; 239/DIG. 12; 128/200.14; 128/203.12; 222/107; 222/215; 222/541.3
(58) Field of Search .......................... 239/1, 327, 462, 239/542, 548, 567, 602, 589, DIG. 12; 128/200.14, 203.12, 203.22; 206/484, 485; 222/94, 103, 206, 107, 215, 482, 484, 541.3

(56) References Cited

U.S. PATENT DOCUMENTS

| | | | |
|---|---|---|---|
| 3,190,499 A | * | 6/1965 | Dow ............................ 206/484 |
| 4,090,642 A | * | 5/1978 | Baker .......................... 206/484 |
| 5,497,763 A | | 3/1996 | Lloyd et al. |
| 5,544,646 A | | 8/1996 | Lloyd et al. |
| 5,660,166 A | | 8/1997 | Lloyd et al. |
| 5,709,202 A | | 1/1998 | Lloyd et al. |
| 5,718,222 A | | 2/1998 | Lloyd et al. |
| 5,823,178 A | | 10/1998 | Lloyd et al. |
| 5,829,435 A | | 11/1998 | Rubsamen et al. |
| 5,906,202 A | | 5/1999 | Schuster et al. |
| 6,070,575 A | * | 6/2000 | Gonda et al. ............ 128/203.12 |
| 6,295,986 B1 | * | 10/2001 | Patel et al. ............. 128/200.14 |
| 6,354,516 B1 | * | 3/2002 | Patel et al. .................. 239/462 |

* cited by examiner

Primary Examiner—Steven J. Ganey
(74) Attorney, Agent, or Firm—Paula A. Borden; Bozicevic, Field & Francis, LLP

(57) ABSTRACT

Methods of generating pores in thin sheets of material, typically thin polymer films, are provided. The methods allow for generation of pores which uniformly penetrate the material. The method comprises laminating a thick film onto a thin film, then directing a laser source onto the thin film so as to form pores through the thin film. The increased stiffness conferred by the thick film reduces wrinkle formation in the thin film, resulting in uniform thickness of the thin film and consequent uniformity of pore depth. The invention further provides aerosolization containers and devices comprising membranes formed according to the invention.

Figure 1:
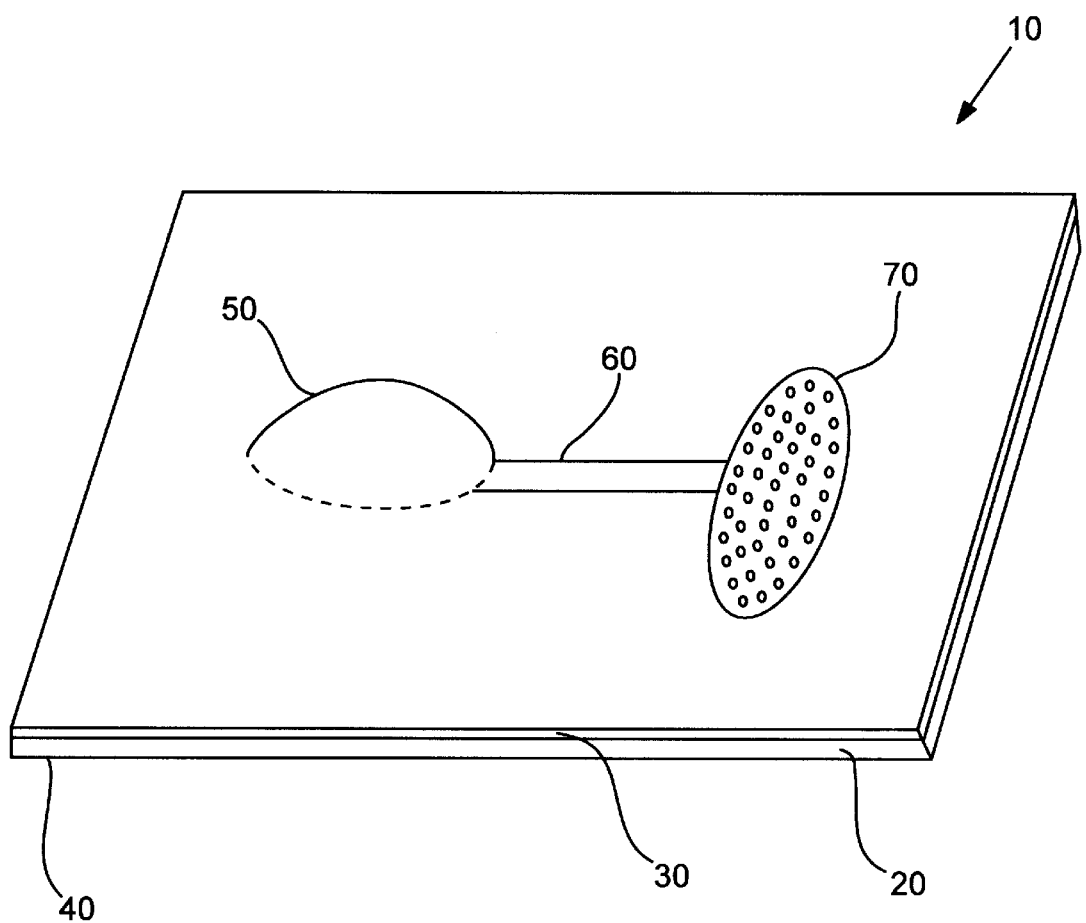

10 Claims, 1 Drawing Sheet

METHOD OF GENERATING UNIFORM PORES IN THIN POLYMER FILMS

FIELD OF THE INVENTION

The present invention relates to methods of generating pores in thin sheets of materials. More particularly, the invention relates to using a laser to drill uniform holes in thin flexible sheets of material comprised of polymers.

BACKGROUND OF THE INVENTION

In various areas of technology it is desirable to make use of a thin sheet of material which has an array of regularly spaced, very small holes therein. For example, such might be used in the manufacture of various electronic components. Thin membranes which have one or more holes in them could also be used in the formation of components used in ink jet printers or fuel injectors. A more direct application of such a porous membrane is as a filter. The pore size and pore density could be adjusted to wide range of filter applications. Alternatively, liquid formulations containing a drug could be moved through such a porous member to create an aerosol for inhalation.

Aerosol therapy can be accomplished by aerosolization of a formulation (e.g., a drug formulation or diagnostic agent formulation) and administration to the patient, for example via inhalation. The aerosol can be used to treat lung tissue locally and/or be absorbed into the circulatory system to deliver the drug systemically. Where the formulation contains a diagnostic agent, the formulation can be used for diagnosis of, for example, conditions and diseases associated with pulmonary dysfunction.

In general, aerosolized particles for respiratory delivery must have a diameter of 12 microns or less. However, the preferred particle size varies with the site targeted (e.g., delivery targeted to the bronchi, bronchia, bronchioles, alveoli, or circulatory system). For example, topical lung treatment can be accomplished with particles having a diameter in the range of 1.0 to 12.0 microns. Effective systemic treatment requires particles having a smaller diameter, generally in the range of 0.5 to 6.0 microns, while effective ocular treatment is adequate with particles having a diameter of 15 microns or greater, generally in the range of 15–100 microns.

U.S. Pat. Nos. 5,544,646; 5,709,202; 5,497,763; 5,544,646; 5,718,222; 5,660,166; 5,823,178; 5,829,435; and 5,906,202 describe devices and methods useful in the generation of aerosols suitable for drug delivery. These devices generate fine, uniform aerosols by passing a formulation through a porous membrane having micron-scale pores as may be formed, for example, by laser ablation.

Porous membranes having such small features are difficult and costly to manufacture. Additionally, the pores must be of high quality and uniformity where they are to be used (1) in manufacturing electronic components; (2) in filter materials; (3) in ink jet printers; (4) in fuel injectors; and (5) to create aerosols for delivering therapeutic agents to patients to insure that the patients consistently receive the therapeutically required dose.

The porous membranes used in various applications are generally very thin, typically less than about a millimeter in thickness. The generation of micron-size holes is achieved by exposing the thin polymer material to a laser beam. Prior to laser drilling, the thin material is typically laminated onto a lid material. During the lamination process, wrinkles are frequently created in the film. The wrinkles frequently result in areas having a thickness greater than the depth of focus of the laser beam. As a consequence, a proportion of the pores drilled only partially penetrate these areas of the membrane. This lack of uniformity in pore formation severely compromises optimal operation of a device incorporating the film. For example, an aerosolization device having such a film incorporated therein requires excessive pressure to force a liquid formulation through the membrane, which can result in failure of the device.

The present invention provides improved methods of making thin porous membranes which do not suffer from the above-mentioned drawbacks, and devices incorporating the membranes.

SUMMARY OF THE INVENTION

Methods of generating pores in thin sheets of material, typically thin polymer films, are provided. The methods allow for generation of pores which uniformly penetrate the material. The method comprises laminating a thick film onto a thin film, then directing a laser source onto the thin film so as to form pores through the thin film. The increased stiffness conferred by the thick film reduces wrinkle formation in the thin film, resulting in uniform thickness of the thin film and consequent uniformity of pore depth. The pores may be formed either individually or simultaneously in one or more groups. The laser source may be controlled using a mask and/or beam-splitting and/or focusing techniques.

The invention further provides a method for generating pore structures in thin polymeric films comprising laminating a thick polymer film onto the thin polymer film, forming a laminate; placing the laminate onto a porous surface such that the thick film side of the laminate is adjacent to the porous surface; applying a vacuum to the porous surface, thereby holding the laminate onto the porous surface; and directing a laser source onto the thin film.

In one aspect of the invention, a neodymium-doped yttrium aluminum garnet (Nd:YAG) laser is used as the laser source.

In another aspect of the invention, an excimer laser is used as the laser source.

In still another aspect of the invention, the pores are formed so as to have an exit aperture of from about 0.5 to about 25 $\mu$m in diameter.

In an additional aspect of the invention, a method of producing a nozzle for aerosolizing a formulation is provided wherein from about 200 to about 1,000 holes are formed in a membrane by projecting an excimer laser or focusing a YAG laser onto the membrane in a manner and for a time sufficient to ablate pores substantially through the membrane. In a particular embodiment, holes having an average relaxed exit aperture diameter of from about 0.5 to about 1.5 $\mu$m and spaced from about 30 to about 70 $\mu$m apart from each other can be formed in the membrane for the formation of particles for aerosol delivery to the respiratory tract.

The present invention further provides films made using the methods of the invention. These films can be used in a variety of devices. In one aspect of the invention, an extrusion nozzle, for use in an aerosolization device, comprising a thin film having pores that uniformly penetrate the thickness of the film is disclosed.

The present invention further provides a container for aerosolizing a flowable liquid formulation for delivery of the aerosolized formulation into a patient, which container comprises a porous membrane made according to a method of the invention. In some embodiments, the container is a blister packet. In some embodiments, the thick polymeric film serves as a barrier in the packet, and is removed just before extrusion of the drug formulation in the blister.

An advantage of the methods of the present invention lies in the property of the films generated by these methods that the majority of pores penetrate the thickness of the film. When these films are used in devices whose use entails extrusion of flowable substances under pressure through the pores, the amount of pressure required to force the flowable substance through the pores in the film is reduced, thereby enhancing the function, reliability, and longevity of the device. A further advantage is that aerosols generated by extruding a flowable formulation through a thin film made according to the methods of the invention are more uniform.

An advantage of the method of the invention is that pores can be formed in the membrane with a reduced number of pulses of applied laser energy.

An advantage of a blister packet made using the methods of the invention is that the thick polymeric film used in the process of generating pores in the thin film can also serve as a part of the blister packet, thereby eliminating the need for additional manufacturing steps.

These and other aspects, objects, features and advantages of the present invention will become apparent to those skilled in the art upon reading this disclosure in connection with the accompanying figure.

BRIEF DESCRIPTIONS OF THE DRAWINGS

FIG. 1 depicts an exemplary embodiment of a blister packet of the invention.

DETAILED DESCRIPTION OF THE INVENTION

Overview of the Invention

The present invention provides methods of generating pores in thin sheets of material, typically thin polymer films. Methods for generating pores in very thin films are known. Generally, these methods involve laminating the thin film onto a lid material, then directing a laser beam, shaped by an aperture, onto the film. Because the films are very thin, during the lamination process, wrinkles are generated in the thin film. When this occurs, "areas of greater thickness," which may exceed the depth of focus of the laser, are formed. The result is that the film will have areas in which the pores do not penetrate the film, with the effect that the actual number of complete pores is reduced. These films are used in a variety of devices whose use entails the use of pressure to force a volume of a flowable substance, such as a liquid or a powder, through the pores in the film. The pressure required to force a given volume of flowable substance through the pores in a film depends, in part, on the number of pores. Formation of incomplete pores effectively reduces the number of complete pores, thus increasing the pressure needed to extrude the volume through the pores. The need to use excessive pressure is undesirable, since it can lead to malfunction of the device.

The present methods provide a solution to this problem by allowing manufacture of very thin films which have a reduced number of incomplete pores compared to films made by previous methods. This is achieved by enhancing the stiffness of the thin film so wrinkle formation is reduced. The methods generally comprise laminating a thick film onto the thin film, then directing laser of a sufficient energy and for a sufficient time at the thin film so that complete pores, i.e. pores that penetrate the thickness of the film, are formed.

The thin films made by the methods of the present invention can be used in a variety of devices.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a formulation" includes mixtures of different formulations, reference to "a pore" includes one or more pores, and reference to "the method" includes reference to equivalent steps and methods known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "porous membrane" and "porous film", used interchangeably herein, refer to a membrane of material having any given outer parameter shape, but preferably having a convex shape, wherein the membrane has a plurality of pores therein, which openings may be placed in a regular or irregular pattern, and which pores have an unflexed diameter of their exit aperture in the range of 0.25 micron to 6 microns and a pore density in the range of 1 to 1,000 pores per square millimeter for respiratory delivery. For ocular delivery, the pores have an unflexed diameter of their exit aperture in the range of 0.5 microns to 50 microns, generally 1.0 to 25 microns, and a similar pore density. The porous membrane has a porosity of about 0.0005% to 0.2%, preferably about 0.01% to 0.1%. In one embodiment, the porous membrane comprises a single row of pores on, e.g., a large piece of membrane material. The pores may be planar with respect to the surface of the porous membrane material, or may have a conical configuration.

The term "complete pore", as used herein, refers to a pore which extends through the entire thickness of a film, i.e., the pore opens onto both surfaces (i.e., entrance surface, to which formulation is applied under pressure, and exit surface, from which formulation is extruded) of the film. The terms "incomplete pore" and "partial pore", used interchangeably herein, refer to a pore which does not open onto both surfaces of the thin film. A pore has an entrance aperture to which a flowable substance is applied under pressure, and an exit aperture, from which flowable substance is extruded. The term "substantially through" with reference to the pores being formed in the membrane or material shall mean pores which either completely traverse the width of the membrane or are formed to have a thin peelable layer over their exit aperture. The pores formed with a peelable layer over their exit apertures are formed so as to peel outward at a substantially lower pressure than would be required to rupture the membrane in the nonporous areas.

The term "porosity" is used herein to refer to a percentage of an area of a surface area that is composed of open space, e.g., a pore, hole, channel or other opening, in a film, membrane, nozzle, filter or other material. The percent porosity is thus defined as the total area of open space divided by the area of the material, expressed as a percentage (multiplied by 100). High porosity (e.g., a porosity greater than 50%) is associated with high flow rates per unit area and low flow resistance. In general, the porosity of the nozzle is less than 10%, and can vary from $10^{-3}\%$ to 10%, while the porosity of the filter is at least 1%, and preferably it is at least 50% porous.

The terms "package" and "disposable package" are used interchangeably herein and refer to a container or two or more containers linked together by an interconnecting means wherein each container preferably includes one or more channels which provide for fluid connection from the container to a nozzle comprised of a porous membrane, which nozzle is preferably not positioned directly over the container, and wherein each container includes at least one surface that is collapsible in a manner so as to allow the forced displacement of the contents of the container through a low resistance filter and out the nozzle (without rupturing the container) in a manner such that the contents are aerosolized. There are at least two variations of the package, depending on whether the drug can be stably stored in a liquid form or must be stored dry and combined with liquid immediately prior to aerosolization.

The contents of each container preferably comprises a formulation, preferably a flowable formulation, more preferably a liquid, flowable formulation, which includes a pharmaceutically active drug or a diagnostic agent. If the drug or diagnostic agent is not liquid and of a sufficiently low viscosity to allow the drug to be aerosolized, the drug or diagnostic agent is dissolved or dispersed in an excipient carrier, preferably without any additional material such as preservatives that might affect the patient. When the contents must be stored in a dry state, the package further includes another container that holds the liquid and can be combined with the dry drug immediately prior to administration.

The term "container" is used herein to refer to a receptacle for holding and/or storing a drug formulation. The container can be single-dose or multidose, and/or disposable or refillable.

The term "formulation" is used herein to refer to any drug or diagnostic agent formulation which is delivered to a patient using the present invention. Such formulations generally include the drug or diagnostic agent present within a pharmaceutically acceptable inert carrier. The formulation is generally in a liquid flowable form which can be readily aerosolized, the particles having a particle size in the range of 0.5 to 12 microns in diameter for respiratory administration. Formulations can be administered to the patient using device of the invention can be administered by nasal, intrapulmonary, or ocular delivery.

The terms "aerosol," "aerosolized formulation," and the like, are used interchangeably herein to refer to a volume of air which has suspended within it particles of a formulation comprising a drug or diagnostic agent wherein the particles have a diameter in the range of 0.5 to 12 microns, for respiratory therapy, or in the range of 15 to 50 microns for ocular therapy.

The terms "formulation" and "flowable formulation" and the like are used interchangeably herein to refer to any pharmaceutically active drug (e.g., a respiratory drug, or drug that acts locally or systemically, and that is suitable for respiratory delivery) or diagnostic agent combined with a pharmaceutically acceptable carrier in flowable form having properties such that it can be aerosolized to particles having a diameter of 0.5 to 12.0 microns for respiratory therapy, or 15 to 75 microns for ocular therapy. Such formulations are preferably solutions, e.g., aqueous solutions, ethanolic solutions, aqueous/ethanolic solutions, saline solutions, colloidal suspensions and microcrystalline suspensions. Preferred formulations are drug(s) and/or diagnostic agent(s) dissolved in a liquid, preferably in water.

The terms "individual", "subject", or "patient", used interchangeably herein, refer to a mammal, generally a human.

Methods of Making Thin Porous Films

The present invention provides methods of producing thin films (also referred to herein as "membranes", which are particularly characterized by being comprised of material which has holes therein. The exit openings of the holes are preferably small and uniform in size such that they permit the generation of uniform sized aerosolized particles of diagnostic and/or therapeutic agents so as to filter out particles above a given size. The films made by these methods have fewer incomplete pores, thus effectively have increased density of pores which extend from the film entrance side to the film exit side, thereby providing conduits for a flowable substance. Because of the increase in effective pore density, films made using the methods of the invention are characterized by the ability to create an aerosol material or a filtering material using less pressure when compared with the pressure needed with films with fewer holes.

The methods of the invention generally comprise laminating a thick film onto a thin film into which holes are to be drilled, thereby forming a laminate having a thin film side and a thick film side; and directing a laser source onto the thin film of the laminate, applying laser energy to the thin film side of the laminate, thereby drilling a plurality of holes which completely traverse the thickness of the thin film.

The thick film, also referred to herein as the "backing", can be laminated onto the thin film using any known method. For the purposes of the present invention, the laminate is so formed that the thin film can be peeled off of the thick film after forming holes in the thin film. The laminate thus formed has a thin film side and a thick film side.

Laser energy of sufficient energy is applied to the thin film side of the laminate for a sufficient amount of time (or number of pulses) such that holes are formed which extend completely through the thin film, as described below.

In some embodiments, the method comprises the steps of laminating a thick film onto a thin film into which holes are to be drilled, thereby creating a laminate having a thick film side and a thin film side; placing the laminate onto a porous sheet such that the thick film side of the laminate is in contact with a first surface of the porous sheet; applying a vacuum to a second surface, opposite the first surface, of the porous sheet, thereby holding the laminate onto the porous sheet; and directing a laser source onto the thin film side of the laminate, applying laser energy onto the thin film side, thereby drilling a plurality of holes which completely traverse the thickness of the thin film. In these embodiments, the porous sheet can be any suitable material that is of sufficient stiffness to provide a support for the laminate, and has sufficient porosity such that a vacuum can be applied to the second surface and hold the laminate in place. The porous sheet can be of any suitable material, including, but not limited to, a porous ceramic material, and a metal material containing pores.

In some embodiments, after drilling the holes in the thin film of the laminate, the thin film is removed from the thick film, and can be used in any suitable device.

In other embodiments, the thin film is not immediately removed from the thick film. In these embodiments, the backing is used as a barrier in a packet for use in an aerosolization device, as described in more detail below.

The method can be carried out using a variety of different lasers, focusing mechanisms, masks or other materials and techniques known to those skilled in the art. Further, the method can be carried out by individually drilling holes within the material or simultaneously drilling groups of holes at the same time. The simultaneous drilling of groups of holes can be carried out using masks and/or beam-splitting or focusing techniques.

Thick Film Dimensions and Materials

The thick film ("backing") increases the stiffness of the thin film, thereby reducing the incidence of wrinkling of the thin film, thus maintaining uniformity of flatness of the thin film. The thick film can be of any material, and is generally less flexible than the thin film. In general, the thickness of the thick film is in the range of from about 25 $\mu$m to about 200 $\mu$m. Thus, the thick film may be from about 25 $\mu$m to about 200 $\mu$m, or from about 50 $\mu$m to about 100 $\mu$m.

The thick film material used may be any material suitable for laminating onto a thin film, including, but not limited to, materials such as polycarbonates, polyimides, polyamides, polysulfone, polyolefin, polyurethane, polyethers, polyether imides, polyethylene and polyesters.

Thin Film Material and Dimensions

The membrane material is preferably hydrophobic and includes, but is not limited to, materials such as polycarbonates, polyimides, polyamides, polysulfone, polyolefin, polyurethane, polyethers, polyether imides, polyethylene and polyesters which may have the pores formed therein by any suitable method including, but not limited to, laser drilling, electron discharge machining, or anisotropic etching through a thin film of metal or other suitable material. Co-polymers of the foregoing can also be used. Shape memory polymers, which are known in the art and have been described in, inter alia, U.S. Pat. No. 5,910,357, can also be used. Preferably, the membrane is one that does not interact chemically with the substance being aerosolized, or the aerosolization solvent. The membrane preferably has sufficient structural integrity so that it is maintained intact (will not rupture) when subjected to force in the amount up to about 580 psi, or, in some embodiments, of up to about 725 psi, while the formulation is forced through the pores.

In some embodiments, the material is a flexible polymeric organic material, for example a polyether, polycarbonate, polyimide, polyether imide, polyethylene or polyester. Flexibility of the material is preferred so that the nozzle can adopt a convex shape and protrude into the airstream upon application of pressure, thus forming the aerosol away from the static boundary layer of air. Material which is substantially non-flexible can also be used, and, if such material is used, is preferably shaped to have a convex configuration.

As would be apparent to those skilled in the art who read this disclosure, the nozzle area is the porous membrane area. That area may be integral with surrounding sheet material (i.e. a porous area of sheet or tape) or be a separate membrane covering an opening in a thin sheet or tape (i.e., a porous membrane sheet separate from the surrounding sheet or tape). In some embodiments, the porous membrane is covered by a removable cover sheet detachably connected to the porous membrane.

The thickness of the membrane affects both the manufacturing of the nozzles and containers as well as the pressure required to generate the desired aerosol during administration. Thinner membranes require less pressure to generate an aerosol, but are conversely more difficult to handle during manufacturing, for example in laminating the membrane to other components of the formulation container. The membrane is preferably about 10 to about 100 $\mu$m in thickness, from about 15 to about 40 micrometers, from about 20 to about 30 micrometers, more preferably from about 12 to about 45 $\mu$m in thickness. In one embodiment, the membrane material is a 25 $\mu$m thick film of polyimide. Considerations for the membrane material include the ease of manufacture in combination with the formulation container, flexibility of the membrane, and the pressure required to generate an aerosol from pores spanning a membrane of a given material, thickness and flexibility.

Pore Sizes and Characteristics

For respiratory delivery, the pores are generally formed so as to have an unflexed exit aperture diameter from about 0.25 to 6.0 micrometers in size, from about 0.5 to 5.0 $\mu$m, and in some embodiments, from about 0.5 to about 2 $\mu$m. When the pores have this size, the droplets that are formed will have a diameter about twice the diameter of the pore size. In some cases, it may be desirable to generate aerosols having an aerodynamic size in a particular range. Thus, it may be of interest to generate particles having an aerodynamic size in the range of 1–3 $\mu$m, 4–6 $\mu$m or 7–10 $\mu$m. Exit pore aperture sizes would be adjusted accordingly.

The pores may be roughly cylindrical or conical in shape, where "cylindrical" means that the pores pass perpendicularly through the membrane and have approximately the same diameter throughout their length, and "conical" means that the pores are larger on one side of the membrane than on the other side, and includes instances where the cross-section of the pores is conical or curved.

The exit aperture size is preferably uniform; following the methods taught herein, the variability in diameter of each hole having a 1.25 $\mu$m aperture is no more than 0.05 $\mu$m, and for a 6 $\mu$m aperture is no more than 0.1 $\mu$m. The nozzle may be provided as an integral part of the formulation packaging, or may be provided separately, for example integrally with the inhalation device, or wound on a roll for disposable use.

For respiratory delivery, the pores are formed so as to have an unflexed exit aperture diameter from about 0.5 to about 6 μm preferably about 1–2 μm. For ocular delivery, the pores are formed so as to have an unflexed exit aperture diameter in the range of 5 microns to 50 microns, preferably 7.5 to 25 microns.

Generally, the pores are spaced about 30 to about 70 μm apart, preferably about 50 μm apart. The spacing is preferably fairly uniform. For ocular delivery, the nozzles are formed so as to have an unflexed exit aperture diameter in the range of about 5 microns to about 50 microns, preferably 7.5 to 25 microns.

The terms "particle diameter", "particle size" and the like are used interchangeably herein to refer to particle size as given in the "aerodynamic" size of the particle. The aerodynamic diameter is a measurement of a particle of unit density that has the same terminal sedimentation velocity in air under normal atmospheric conditions as the particle in question. When small (e.g., 1–50 micrometer diameter) particles are said to have the same diameter, they have the same terminal sedimentation velocity. This is pointed out in that it is difficult to accurately measure the diameter of small particles using current technology and the shape of such small particles may be continually changing. For ocular delivery, the pores are formed so as to have an unflexed exit aperture diameter in the range of 5 microns to 50 microns, preferably 7.5 to 25 microns.

The pores can be spaced from about 10 to about 1000 μm apart or more, but are preferably spaced from about 30 to about 70 μm apart, most preferably about 50 μm apart. The pore spacing is determined in part by the need to prevent the aerosol from adjacent pores from adversely interfering with each other, and in part to minimize the amount of membrane used and the associated manufacturing difficulties and costs. The pore spacing is preferably fairly uniform, with a variability in the interpore distance of preferably less than about 20%, more preferably less than about 10%, and most preferably about 2% or less (<1 μm variability for pores spaced 50 μm apart).

The pores in a nozzle area may be arranged in regular arrays, such as in rows or grids of pores at regular, substantially uniform distances from one another. In one embodiment of the invention, the pores are formed in a 7×48 array of pores spaced 50 μm apart.

A given membrane may have a plurality of nozzle areas, at a given distance from an adjacent nozzle area, and separated from adjacent nozzle area by a section of non-porous membrane. In some embodiments, the membrane is a strip comprising a plurality of nozzle areas separated from one another by non-porous membrane areas.

The amount of liquid being aerosolized is generally from about 10 μm to about 100 milliliters. In some embodiments, the amount of liquid is in a range of from about 5 milliliters (ml) to about 100 milliliters, from about 10 milliliters to about 90 milliliters, from about 20 milliliters to about 80 milliliters, from about 40 milliliters to about 60 milliliters. In other embodiments, the amount of liquid is in a range of from about 0.5 ml to about 10 ml, from about 1 ml to about 8 ml, from about 2 ml to about 6 ml. In still other embodiments, the amount of liquid is in a range of from about 10 μl to about 1000 μl, from about 20 μm to about 100 μl.

The density of pores in the nozzle area ranges from 1 to about 1,000 pores, generally about 100 to about 900 pores, per square millimeter. In some embodiments, the pore density in the nozzle area is about 100 pores per square millimeter. In other embodiments, this density is about 200 pores per square millimeter.

The period of time over which the formulation is to be administered must also be considered. The delivery time is a critical parameter, as it is necessary to generate the aerosol during a sufficiently short period of time so that the aerosol may be targeted to a specific area of the respiratory tract during inspiration. For a given pore exit diameter and formulation pressure, hole number can be adjusted to control delivery time. Generally, aerosolization will occur within about 0.5 to about 5 seconds, usually in a range of about 1 second to about 2 seconds.

In one embodiment, the pores are incompletely formed so that a thin peelable layer remains covering the exit apertures of the pores. This peelable layer bursts outward upon forcible application of the drug formulation to the nozzle during drug delivery, permitting aerosolization of the formulation. The peelable layer of the pores is formed so as to have a breaking pressure significantly below that of the overall membrane, and the pressure at which the layer bursts is significantly below that applied in the normal course of drug administration, so that the pores burst substantially uniformly and completely. The incompletely formed pores may be formed by application of a thin layer of material to the outer side of the membrane after formation of complete pores, or by incompletely ablating holes through the membrane.

Laser Source

The particular laser source used in the method of the invention will to some extent be determined by the material in which the pores are to be formed. Generally, the laser source must supply a sufficient amount of energy of a wavelength which can form an effective aerosolization nozzle in the material being ablated. Typically the wavelength can be from about 150 to about 360 nm.

The output of the particular laser source can be manipulated in a variety of ways prior to being applied to the material. For example, the frequency can be doubled or tripled using, for example, a lithium triborate crystal or series of crystals using a type I process, a type II process or a combination thereof. This laser beam can be further split into multiple beams to create multiple pores simultaneously. The beam can also be directed through a mask or spatially filtered, and can also be expanded prior to focusing.

One laser effective for such nozzles is a neodymium-yttrium aluminum garnet laser. This laser is a pulsed ultraviolet wavelength light source which provides sufficiently high peak power in short pulses to permit precise ablation in a thin material. The beam profile from this laser is radially symmetric which tends to produce radially symmetric pores.

Another laser effective for creating pores in materials such as polyethers and polyimides is an excimer laser. This laser produces ultraviolet wavelength light, similar to the Nd:YAG laser. However, the beam is not radially symmetrical but can be projected through a mask to simultaneously drill one or more conical or cylindrical holes. Preferably, the laser source is an excimer laser providing a wavelength of 308 nm.

The number of pulses and/or the energy required to form uniform, complete pores according to the method of the present invention is generally reduced, due to the uniformity in thickness of the membrane in which pores are being formed. Thus, the energy density used for a laser typically ranges from about 300 to about 800 mJ/cm$^2$, or from about 525 to about 725 mJ/cm$^2$, and in many embodiments is about 630 mJ/cm$^2$. Using such a laser on a 25 μm thick polyimide membrane, the number of pulses is generally in the range of from about 80 to about 300, or from about 100 to about 200, and in many embodiments is about 120 pulses.

Aerosolization Containers and Devices

The present invention further provides aerosol delivery containers and devices which comprise an aerosolization nozzle as described herein.

In general, a container for aerosolizing a flowable liquid formulation for delivery into a patient comprises: (a) a sheet of membrane material having an entrance side to which a flowable liquid formulation is applied under a pressure, an exit side from which aerosol is released, and a nozzle area, which nozzle area has a plurality of pores therein through which said formulation is extruded, wherein the flexible membrane material is formed by the method according to the present invention; (b) container walls connected to the sheet wherein a wall is collapsible by the application of a force; and (c) a liquid formulation held within the container walls.

The membrane material may be a flexible membrane material. In some embodiments, the membrane material is a laminate formed by the method according to the invention.

In some embodiments, the container is a blister packet. In particular embodiment, the container is a blister packet such as the one depicted in FIG. 1.

In general, aerosol delivery devices useful with the invention comprise (a) a device for holding a formulation-containing container as described above, which container is preferably a disposable container, with at least one but preferably a number of containers, and (b) a mechanical mechanism for forcing the contents of a container (on the package) through a nozzle comprised of a porous membrane as provided by the present invention, optionally preceded by a low resistance filter. Where the device is used for respiratory delivery, the device can further comprise (c) a means for controlling the inspiratory flow profile, (d) a means for controlling the volume in which the drug or diagnostic agent is inhaled, (e) a switch for automatically releasing or firing the mechanical means to release a determined volume of aerosol and aerosol-free air when the inspiratory flow rate and/or volume reaches a predetermined point, (f) a means for holding and moving one package after another into a drug release position so that a new package is positioned in place for each release of drug, and (g) a source of power, e.g., spring, or conventional batteries or other source of electric power.

Examples of preferred inhalation devices for use in conjunction with the aerosolization nozzles of the present invention are those described in U.S. Pat. Nos. 5,622,162; 5,608,647; 5,934,272; 5,915,378; 5,906,202, incorporated herein by reference.

The invention provides a method for fabricating a porous membrane useful for delivering any type of formulation, including drug or diagnostic agent formulations, to a patient by ocular administration or inhalation in the form of an aerosol having a desired aerosol particle size and having substantially no undesirable particles within the aerosol that would substantially affect the accuracy of the dose of drug or diagnostic agent delivered in the aerosol. Moreover, certain embodiments of the devices and methodology used do not require the release of low boiling point propellants in order to aerosolize drug, which propellants are conventionally used in connection with hand-held metered dose inhalers. However, like conventional hand-held metered dose inhalers, the devices used in conjunction with the present invention can be hand-held, self-contained, highly portable devices which provide a convenient means of delivering drugs or diagnostic agents to a patient.

In general, an aerosol for respiratory or ocular delivery is generated from a drug or diagnostic agent formulation, preferably a flowable formulation, more preferably a liquid, flowable formulation. The drug or diagnostic agent formulation can be contained within a multidose container or within a container portion of a disposable package, where the container of the disposable package has at least one surface that is collapsible. The aerosol is generated by applying pressure of 800 pounds per square inch (psi) or less, 700 psi or less, 600 psi or less, or 500 psi or less, to the collapsible container surface, thereby forcing the contents of the container through a nozzle array comprised of a porous membrane. Alternatively, the formulation is first forced through a low resistance filter and then through the porous membrane. The porous membrane may be rigid or flexible. Preferably the porous membrane is flexible so that upon application of the pressure required to aerosolize the formulation, the nozzle's porous membrane becomes convex in shape, thus delivering the aerosolized drug or diagnostic agent into the flow path of the delivery device in a region beyond the flow boundary layer. The low resistance filter, if present, has a porosity the same as or preferably greater than the porosity of the porous membrane to provide for an overall flow resistance that is preferably lower than the flow resistance of the nozzle. The low resistance filter thus prevents particles of an undesirable size from reaching the nozzle, thereby reducing clogging of the nozzle from the inside, and filters out such undesirable particles before the aerosol for delivery is generated, thereby avoiding delivery of undesirable particles to the patient.

The formulations for aerosolization can include preservatives or bacteriostatic type compounds. However, the formulation preferably comprises a pharmaceutically active drug (or a diagnostic agent) and a pharmaceutically acceptable carrier such as water. The formulation can be primarily or essentially composed of the drug or diagnostic agent (i.e., without carrier) if the drug or diagnostic agent is freely flowable and can be aerosolized. Useful formulations include, for example, formulations currently approved for use with nebulizers or for injections.

In general, the low-resistance filter and nozzle comprised of a porous membrane formed according to the invention can be used in conjunction with any container suitable for containing a drug or diagnostic agent formulation of interest. The container can be, for example, a single-dose container or a multidose container. The containers can be refillable, reusable, and/or disposable. Preferably, the container is disposable. The container can be designed for storage and delivery of a drug or diagnostic agent that is dry, substantially dry, liquid, or in the form of a suspension. The container may be any desired size. In most cases the size of the container is not directly related to the amount of drug or diagnostic agent being delivered in that most formulations include relatively large amounts of excipient material, e.g., water or a saline solution. Accordingly, a given size container could include a wide range of different doses by varying drug (or diagnostic agent) concentration.

The container can also be one that provides for storage of a drug or diagnostic agent in a dry or substantially dry form until the time of administration, at which point, if desired, the drug or diagnostic agent can be mixed with water or other liquid. An exemplary dual compartment container for carrying out such mixing of dry drug with liquid just prior to administration is described in U.S. Pat. No. 5,709,202 issued Jan. 20, 1998, incorporated herein by reference with respect to such containers.

In a preferred embodiment, the containers useful with the invention comprise a single-use, single-dose, disposable container that holds a formulation for delivery to a patient and has a collapsible wall. In addition, the container can be configured in the same package with a porous membrane and a low resistance filter, where the low resistance filter is positioned between the porous membrane and a formulation contained in the container. The container is preferably disposable after a single use in the delivery of the formulation contained therein.

The low resistance filter and the nozzle can be included as components of a disposable package that is composed of a container that serves as a storage receptacle for the drug formulation, a porous membrane, and a low resistance filter positioned between the drug formulation and the nozzle.

The low resistance filter and the nozzle can also be provided separate from the drug container and/or the disposable package. For example, the low resistance filter can be provided as a single disposable filter that can be inserted in the proper position between the formulation in the container and a nozzle, which can also be provided as a single disposable unit. The disposable filter and disposable nozzle can be inserted prior to use and can be disposed after each use or after a recommended number of uses. Alternatively, the low resistance filter and nozzle can be provided as a separate ribbon or ribbons. Such filters are described and disclosed in U.S. Pat. No. 5,829,435 issued Nov, 3, 1998.

Turning now to the figure, FIG. 1 depicts an exemplary embodiment of the invention in which the thick film 20 is used as a barrier in a blister packet 10. The thick film 20 has high barrier properties for oxygen, and is laminated to the thin film 30, forming a laminate 40. The laminate is drilled using an excimer laser, as described above. The thick film 20 is not removed after laser ablation. During manufacture of the blister packet 10, the blister material is heat-sealed only in the area outside the dotted line shown in FIG. 1, i.e., outside the blister 50, flow channel 60, and nozzle 70. The heat seal is performed in such a way that the peel strength is more than about 800 psi. The thick film 20 is left on the packet and is removed just before extrusion of the flowable substance from the blister 50, through the flow channel 60, and through the nozzle 70. In this method, there is no requirement to open the flow channel where the liquid travels from the blister to the nozzle. Since the pressure required to produce the aerosol is less than about 600 psi, there is also no need to clamp the packet around the blister and flow channel.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit, and scope of the present invention. All such modifications are intended to be within the scope of the claims appended hereto.

What is claimed is:

1. A method of producing a porous membrane, the method comprising the steps of:
    (a) laminating a thick film onto a thin film, forming a laminate having a thick film side and a thin film side;
    (b) placing said laminate onto a porous sheet such that said thick film side of said laminate is in contact with a first surface of said porous sheet;
    (c) applying a vacuum to a second surface opposite said first surface of said porous sheet, thereby holding said laminate onto said first surface; and
    (d) directing laser energy onto the thin film of the laminate until the laser has created a plurality of pores in the thin film.

2. The method of claim 1, wherein at least about 90% of the pores are complete.

3. The method of claim 1, wherein the thin film has a thickness in the range of about 10 $\mu$m to about 100 $\mu$m.

4. The method of claim 1, wherein the thick film has a thickness in the range of about 25 $\mu$m to about 200 $\mu$m.

5. The method of claim 1, wherein said porous sheet is ceramic.

6. The method of claim 1, wherein the laser source is a UV excimer laser having a wavelength of 308 nm.

7. The method of claim 1, wherein the excimer energy density is from about 525 to about 725 mJ/cm$^2$.

8. The method of claim 1, wherein the laser source is a neodymium-yttrium aluminum garnet laser providing a beam having a wavelength of 355 nm.

9. The method of claim 1, wherein from about 0.1 to about 10 mW of power is provided by said laser.

10. The method of claim 1, wherein the membrane is comprised of a material selected from the group consisting of polycarbonates, polyimides, polyethers, polyether imides, polyethylene and polyesters.

* * * * *